United States Patent [19]

Cartwright et al.

[11] 4,133,674

[45] Jan. 9, 1979

[54] HERBICIDAL HETEROCYCLIC COMPOUNDS

[75] Inventors: David Cartwright, Reading; Philip L. Urlwin-Smith, Sunninghill, both of England

[73] Assignee: Imperial Chemical Industries Limited, London, England

[21] Appl. No.: 793,271

[22] Filed: May 3, 1977

[30] Foreign Application Priority Data

May 12, 1976 [GB] United Kingdom ............... 19488/76

[51] Int. Cl.$^2$ ...................... A01N 9/22; C07D 251/08
[52] U.S. Cl. ......................................... 71/93; 544/212
[58] Field of Search ............................. 71/93; 544/212

[56] References Cited

U.S. PATENT DOCUMENTS 3,759,910  9/1973  Dickore et al. .......................... 71/93
3,907,796  9/1975  Jewell et al. ............................. 71/93

Primary Examiner—Catherine L. Mills
Attorney, Agent, or Firm—Cushman, Darby & Cushman

[57] ABSTRACT

Herbicidal compounds of formula:

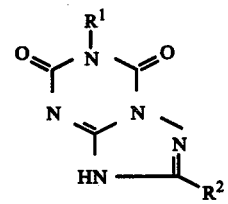

and their salts, wherein $R^1$ and $R^2$ are specified alkyl groups, potentially useful as selective herbicides for cereals.

10 Claims, No Drawings

HERBICIDAL HETEROCYCLIC COMPOUNDS

This invention relates to herbicidal processes and herbicidal compositions, and chemical compounds useful therein.

According to the present invention there is provided a process of severely damaging or killing unwanted plants, which comprises applying to the plants, or to the growth medium thereof, a triazolotriazine compound of the formula (I):

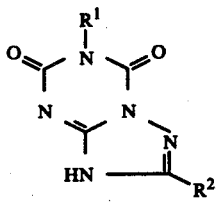

or a salt thereof, wherein $R^1$ is an alkyl or cycloalkyl radical of 1 to 8 carbon atoms and $R^2$ is a hydrogen atom; an alkyl or cycloalkyl radical of 1 to 6 carbon atoms; an alkylthio radical of 1 to 6 carbon atoms; or a dialkylamino radical wherein the alkyl radicals each contain from 1 to 6 carbon atoms.

When $R^1$ is an alkyl radical it may be for example a straight or branched chain alkyl radical, or a cycloalkyl radical. Thus, $R^1$ may be, for example, a methyl, ethyl, propyl, isopropyl, cyclopropyl, n-butyl, sec-butyl, isobutyl, cyclopentyl, neopentyl or cyclohexyl radical. Preferably $R^1$ is an isopropyl, sec-butyl or cyclopropyl radical. When $R^2$ is an alkyl radical it may be, for example, a straight or branched chain alkyl radical, or a cycloalkyl radical. Thus, $R^2$ may be, for example, a methyl, ethyl, propyl, isopropyl, cyclopropyl, butyl, sec-butyl, t-butyl, or isobutyl radical.

Preferred compounds for use in the process of the invention include those in which $R^1$ is an isopropyl radical. Particular examples of preferred compounds for use in the invention include compounds no. 1 and no. 4 of Table I below.

The compounds of the foregoing structural formula (I) contain an N-H group. The hydrogen atom of this group is acidic and may be replaced by salt-forming bases, for example by alkali or alkaline earth metal cations. Accordingly, the compounds of formula (I) may be converted for example into their sodium, potassium, calcium, or magnesium salts. Other examples of cations which may be used to prepare salts of the compounds (I) include the ammonium ion and substituted ammonium ions, for example ammonium ions substituted by one, two, three, or four alkyl radicals, each of 1 to 6 carbon atoms. Preferred cations are sodium and potassium cations.

The foregoing structural formula (I) is considered to be the most appropriate to represent the structure of the compounds used in the process of the invention. However, compounds of this type are capable, in principle, of existing in at least one alternative tautomeric form having the following formula (II):

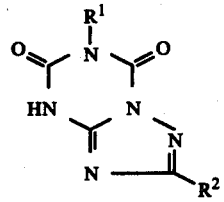

The formula (I) given above is to be considered inclusive of and representative of all tautomeric structures such as (II).

Particular examples of compounds useful in the process of the invention are listed in Table I below.

TABLE I

| COMPOUND NO | $R^1$ | $R^2$ | MELTING POINT °C |
|---|---|---|---|
| 1 | iso $C_3H_7$ | iso $C_3H_7$ | 156-159 |
| 2 | $CH_3$ | iso $C_3H_7$ | 214 |
| 3 | $C_3H_7$ | iso $C_3H_7$ | 112 |
| 4 | iso $C_3H_7$ | $CH_3$ | 202 |
| 5 | iso $C_3H_7$ | $C_2H_5$ | 185 |
| 6 | iso $C_3H_7$ | $C_3H_7$ | 175 |
| 7 | $C_3H_7$ | $CH_3$ | 225 |
| 8 | $C_2H_5$ | iso $C_3H_7$ | 157 |
| 9 | $C_2H_5$ | $CH_3$ | 236 |
| 10 | cyclo $C_6H_{11}$ | $CH_3$ | over 260 |
| 11 | sec $C_4H_9$ | $C_2H_5$ | 125 |
| 12 | iso $C_4H_9$ | iso $C_3H_7$ | 145 |
| 13 | neo $C_5H_{11}$ | $CH_3$ | 194 |
| 14 | sec $C_4H_9$ | $CH_3$ | 160 |
| 15 | neo $C_5H_{11}$ | $C_2H_5$ | 171 |
| 16 | iso $C_4H_9$ | $C_2H_5$ | 125 |
| 17 | neo $C_5H_{11}$ | iso $C_3H_7$ | 186 |
| 18 | cyclo propyl | iso $C_3H_7$ | 154 |
| 19 | isopropyl | H | 216 |
| 20 | isopropyl | t $C_4H_9$ | 128 |
| 21 | sec $C_4H_9$ | t $C_4H_9$ | 139 |
| 22 | sec $C_4H_9$ | iso $C_3H_7$ | 125 |
| 23 | cyclo $C_3H_5$ | iso $C_3H_7$ | 217 |
| 24 | iso $C_3H_7$ | $CH_3S-$ | 260 |
| 25 | iso $C_3H_7$ | $(CH_3)_2N-$ | 220 |

The compounds used in the process of the invention include compounds which are effective to severely damage or to kill unwanted plants both when applied directly to the plants ("post-emergence application") and when applied to soil or other growth medium to prevent the emergence of seedlings of unwanted plants ("pre-emergence application"). The rate of application required to severely damage or kill unwanted plants will depend upon the identity of the plants and upon the particular compound chosen for use. By way of general guidance, however, a rate of from 0.5 to 10 kilograms per hectare is generally suitable while from 1 to 4 kilograms is often preferred.

When applied directly to plants (i.e. post-emergence application) the compounds used in the process of the invention are relatively less phytotoxic towards cultivated cereals, for example, maize, wheat, and barley than they are towards many other species of plants. Accordingly, the compounds may be used to control weeds growing in the latter crops.

In addition to controlling broad-leaved weeds, the compounds of the invention also show damaging herbicidal effects against wild oats, at rates of application which do not substantially injure wheat or barley. In a further aspect, therefore, the invention provides a process of selectively inhibiting the growth of weeds, including wild oats, in crops of wheat and barley, which comprises applying to the area of the crop a triazolotriazine compound according to formula (I) above, in an amount sufficient to inhibit the growth of the weeds, but insufficient to damage the crop substantially. The rate at which the compound is to be applied will depend upon the particular compound chosen for use, but by way of general guidance, a rate of from 0.5 to 5 kilograms per hectare is generally suitable.

A particularly preferred compound for controlling wild oats growing in wheat or barley is compound no. 4 of Table I.

The compounds used in the process of the invention may also be used as selective herbicides to control weeds growing in peanut crops, when applied at an early stage of growth of the peanut crop.

The compounds used in the process of the invention are preferably applied in the form of a composition, in which the active ingredient is mixed with a diluent or carrier. In another aspect, therefore, the invention provides a herbicidal composition, comprising as an active ingredient a compound of formula (I) or a metal, ammonium, or substituted ammonium salt thereof, in admixture with a solid or liquid diluent. Preferably the composition further comprises a surface-active agent.

The solid compositions of the invention may be, for example, in the form of dusting powders, or may take the form of granules. Suitable solid diluents include, for example, Kaolin, bentonite, kieselguhr, dolomite, calcium, carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. One form of liquid composition according to the invention comprises an aqueous solution of an alkali metal salt of a triazolotriazine compound as hereinbefore defined. The choice of a surface-active agent for use in the compositions of the invention will be within the competence of one skilled in herbicide technology. By way of example, however, it may be noted that spray compositions ready for application in the field have been prepared which comprise a solution of the sodium salt of compound no. 4 of Table I in water containing 1 gram per liter of Ortho X-77, a blend of surfactants containing alkylarylpolyoxyethylene glycols together with free fatty acids and isopropanol. A spray composition containing the sodium salt of compound no. 4 in water containing 6 grams per liter of Atplus has also been prepared; Atplus is a herbicidal adjuvant comprising an emulsifiable oil. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic monoesters of sulphuric acid, for example sodium lauryl sulphate; and salts of sulphonated aromatic compounds, for example dodecylbenzenesulphonate, sodium, calcium and ammonium lignosulphonate, butylnaphthalene sulphonate, and a mixture of the sodium salts of diisopropyl- and triisopropylnaphthalenesulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

The compositions which are to be used in the form of aqueous solutions, dispersions or emulsions are generally supplied in the form of a concentrate containing a high proportion of the active ingredient, the concentrate being diluted with water before use. These concentrates are usually required to withstand storage for prolonged periods and after such storage to be capable of dilution with water in order to form aqueous preparations which remain homogeneous for a sufficient time to enable them to be applied by conventional spray equipment. In general concentrates may conveniently contain from 10 to 85% and preferably from 25 to 60% by weight of active ingredient. Dilute preparations ready for use may contain varying amounts of the active ingredients, depending upon the purpose for which they are to be used; however, dilute preparations suitable for many uses contain between 0.01 and 10% and preferably between 0.1 and 1% by weight of the active ingredient.

In another aspect, the invention provides herbicidal triazolotriazine compounds of the foregoing formula (I) and salts, thereof.

The compounds (I) provided by the invention may be prepared according to the following reaction scheme (A).

Scheme A

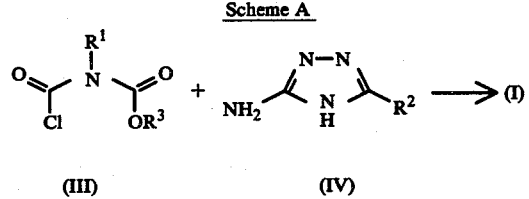

According to scheme A, an N-substituted-N-chlorocarbonyl urethane derivative (III) is reacted with a 5-substituted-3-amino-1,2,4-triazole (IV). The reaction is preferably carried out in an inert diluent or solvent for the reactants.

The N-chlorocarbonyl derivative is prepared by reaction of a urethane

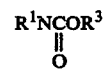

with carbonyl chloride in a diluent, preferably toluene. The symbol $R^1$ has the meaning previously assigned to it in this specification. The symbol $R^3$ stands for a lower alkyl radical, preferably a methyl group. The triazole derivative (IV) may be a known compound or may be prepared by methods analogous to those used for known compounds, for example by reaction of an acid

with aminoguanidine as shown below.

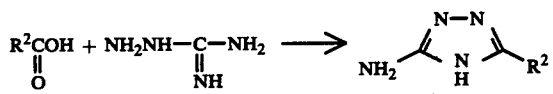

The structure of the products prepared by Scheme A has been confirmed by preparing compound no. 4 of Table I by an alternative unambiguous route and confirming that the product was identical with compound no. 4 prepared by the method of Scheme A.

An alternative convenient procedure for preparing the compounds of the invention is shown below in Scheme B.

Scheme B

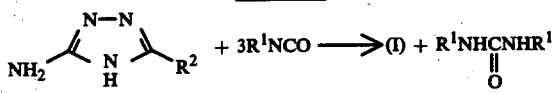

In scheme B, a suitably substituted 3-amino-1,2,4-triazole is reacted with three molar proportions of an appropriate isocyanate to give the compounds (I) used in the invention. In Scheme B, the symbols $R^1$ and $R^2$ have any of the meanings previously assigned to them. The process of Scheme B is preferably carried out in a diluent. Examples of diluents include pyridine and alkyl pyridines. The reaction is preferably carried out at an elevated temperature, for example from 100° C to 150° C. Conveniently, the reaction may be performed at the boiling point of pyridine (i.e. ca. 115° C).

A further procedure for preparing the compounds of the invention is shown in Scheme C.

Scheme C

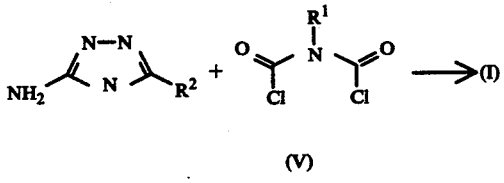

In Scheme C, a suitably substituted 3-amino-1,2,4-triazole is reacted with a bis-chloroformyl compound (V). The reaction is preferably carried out in an inert diluent or solvent for the reactants. Examples of diluents include liquid hydrocarbons, for example toluene, and aprotic solvents, for example acetonitrile.

The invention is illustrated by the following Examples, in which all parts are by weight and all temperatures are in degrees Centigrade unless otherwise stated.

EXAMPLE 1

This Example illustrates the herbicidal properties of the compounds used in the process of the invention. Each compound (0.12 g) was formulated for test by mixing it with 5 ml of an emulsion prepared by diluting 100 ml of a solution containing 21.8 grams per liter of Span 80 and 78.2 grams per liter of Tween 20 in methyl cyclohexanone to 500 ml with water. Span 80 is a Trade Mark for a surface-active agent comprising sorbitan monolaurate. Tween 20 is a Trade Mark for a surface-active agent comprising a condensate of twenty molar proportions of ethylene oxide with sorbitan monooleate. The mixture of the compound and the emulsion was shaken with glass beads and diluted to 12 ml with water.

The spray composition so prepared was sprayed on to young pot plants (post-emergence test) of the species named in Table II below, at a rate equivalent to 1000 liters per hectare (10 kilograms of triazine compound per hectare). Damage to plants was assessed 14 days after spraying by comparison with untreated plants, on a scale of 0 to 3 where 0 is no effect and 3 represents 75 to 100% kill. In a test for pre-emergence herbicidal activity, seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 3. The results are given in Table II below:

TABLE II

| Compound No | PRE- OR POST-EMERGENCE APPLICATION | TEST PLANTS | | | | | |
|---|---|---|---|---|---|---|---|
| | | Le | To | Ot/Av | Dg | Pr | Cp |
| 2 | Pre | 0 | 1 | 0 | 2 | 1 | 0 |
|   | Post | 2 | 0 | 0 | 2 | 0 | 0 |
| 3 | Post | 2 | 3 | 0 | 0 | 0 | 0 |
| 4 | Pre | 2 | 2 | 0 | 3 | 0 | 1 |
|   | Post | 3 | 3 | 3 | 2 | 2 | 1 |
| 5 | Post | 3 | 3 | 2 | 0 | 0 | 0 |
| 6 | Post | 3 | 3 | 0 | 0 | 0 | 0 |
| 7 | Pre | 3 | 1 | 1 | 1 | 0 | 0 |
|   | Post | 3 | 1 | 0 | 0 | 0 | 0 |
| 8 | Pre | 3 | 1 | 0 | 1 | 0 | 0 |
|   | Post | 3 | 3 | 1 | 0 | 0 | 0 |
| 9 | Pre | 0 | 0 | 0 | 0 | 0 | 3 |
|   | Post | 3 | 2 | 0 | 0 | 0 | 0 |
| 10 | Pre | 0 | 0 | 0 | 0 | 0 | 0 |
|    | Post | 3 | 1 | — | 0 | 0 | 0 |
| 11 | Pre | 0 | 0 | 0 | 0 | 0 | 0 |
|    | Post | 3 | 3 | 0 | 0 | 0 | 0 |
| 12 | Post | 3 | 3 | 0 | 3 | 1 | 0 |
| 13 | Post | 3 | 3 | 1 | 1 | 1 | 0 |
| 14 | Post | 3 | 3 | 2 | 3 | 2 | 0 |
| 15 | Post | 1 | 3 | 0 | 3 | 1 | 0 |
| 16 | Post | 2 | 3 | 0 | 0 | 0 | 0 |
| 17 | Post | 1 | 3 | 0 | 3 | 0 | 0 |
| 18 | Post | 3 | 3 | 0 | 2 | 2 | 0 |
| 19 | Post | 2 | 3 | 2 | 1 | 0 | 0 |
| 20 | Pre | 3 | 1 | 0 | — | 3 | 0 |
|    | Post | 3 | 3 | 1 | 3 | 2 | 0 |
| 21* | Pre | 3 | 0 | 0 | — | 0 | 0 |
|     | Post | 3 | 3 | 3 | 2 | 1 | 0 |
| 23 | Post | 3 | 3 | — | — | 0 | 0 |
| 24 | Post | 3 | 3 | 0 | — | 0 | 0 |
| 25 | Pre | 1 | 0 | 2 | — | 0 | 0 |
|    | Post | 0 | 3 | 2 | — | 2 | 0 |

*Applied at 5 kilograms per hectare

Compounds 3, 5, 6, 10 to 19, 21 and 22 to 25 showed no significant herbicidal activity in the pre-emergence test.

The names of the test plants are as follows:
Le Lettuce
To Tomato
Ot/Av Cultivated oats and wild oats (*Avena fatua*). Wild oats are used in the post-emergence test and cultivated oats in the pre-emergence test.
Dg *Digitaria sanguinalis*
Pr Perennial ryegrass (*Lolium perenne*)
Cp *Cyperus rotundus*

EXAMPLE 2

TABLE III

| Compound No | Rate of Application (kg/ha) | Pre- or Post-Emergence Application | sb | Rp | Ct | Sy | Mz | Ww | Rc | Sn | Ip | Am | Pi | Ca | Po | Ab | Cv | Ot/Wo | Dg | Pu | St | Ec | Sh | Ag | Cn |
|---|---|---|---|---|---|---|---|---|---|---|---|---|---|---|---|---|---|---|---|---|---|---|---|---|---|
| 3 | 5 | Post | 2 | 2 | 0 | 2 | 0 | 0 | 0 | 2 | 0 | 2 | 1 | 4 | — | 2 | 2 | 0 | 0 | 0 | 0 | 0 | 0 | 0 | 0 |
| 4 | 1 | Post | 4 | 4 | 2 | 3 | 0 | 0 | 1 | 5 | 5 | 4 | 4 | 5 | 5 | 5 | 4 | 2 | 1 | 3 | 5 | 4 | 0 | 0 | 0 |
|   | 5 | Pre | 5 | 1 | 1 | 4 | 0 | 3 | 2 | 3 | 3 | 4 | 4 | 3 | 4 | 5 | — | 4 | 1 | 0 | 2 | 0 | — | 0 | 0 |
| 5 | 5 | Pre | 5 | 0 | 0 | 0 | 0 | 3 | 3 | 0 | 0 | 2 | 4 | 4 | 4 | 4 | — | 5 | 0 | 0 | 0 | 0 | — | — | 0 |
|   | 5 | Post | 5 | 2 | 2 | 2 | 0 | 2 | 0 | 5 | 5 | 4 | 5 | 5 | 5 | 5 | 3 | 0 | 0 | 1 | 0 | 0 | 0 | 1 | 0 |
| 8 | 5 | Pre | 4 | 0 | 0 | 0 | 0 | 2 | 0 | 2 | 0 | 1 | 1 | 0 | 0 | 2 | — | 1 | 0 | 0 | 1 | 1 | — | — | 0 |
|   | 5 | Post | 5 | 4 | 3 | 4 | 0 | 0 | 0 | 5 | 4 | 3 | 5 | 5 | 4 | 4 | 2 | 0 | 0 | 0 | 1 | 0 | 0 | 0 | 0 |
| 9 | 5 | Post | 0 | 1 | 0 | 0 | 0 | 0 | 0 | 3 | 2 | 2 | 3 | 4 | 3 | 1 | 2 | 0 | 0 | 0 | 0 | 0 | 0 | 0 | 0 |
| 14 | 1 | Post | 4 | — | — | 3 | 0 | — | 4 | 4 | 5 | — | 3 | 5 | 5 | 4 | 2 | 2 | 1 | — | 0 | — | 0 | 0 | 0 |
| 15 | 5 | Post | 2 | — | — | 3 | 0 | — | 1 | 1 | 1 | — | 1 | 2 | 4 | 0 | 2 | 1 | 0 | — | 0 | — | 0 | 0 | 0 |
| 18 | 5 | Pre | 5 | 4 | 0 | 1 | 0 | 2 | 0 | 0 | 1 | 3 | 3 | 4 | 3 | 5 | — | 4 | 0 | 0 | 0 | 3 | — | 0 | 0 |
|   | 5 | Post | 5 | 5 | 4 | 4 | 0 | 0 | 0 | 5 | 4 | 5 | 5 | 5 | 5 | 4 | 4 | 2 | 4 | 0 | 1 | 5 | 0 | 0 | 0 |
| 6 | 0.05 | Pre | 5 | 0 | 0 | 0 | 0 | 4 | 0 | 2 | 0 | 2 | 1 | 0 | 0 | 2 | — | 1 | 1 | 1 | 2 | 1 | — | — | 0 |
|   |   | Post | 3 | 3 | 3 | 3 | 0 | 0 | 0 | 5 | 3 | 3 | 4 | 4 | 0 | 5 | 0 | 0 | 0 | 0 | 0 | 0 | 0 | 0 | 0 |
| 11 | 0.05 | Pre | 5 | 2 | 0 | 1 | 1 | 0 | 3 | 3 | 3 | — | 0 | 0 | 0 | 1 | — | 0 | 1 | 1 | 1 | 1 | — | 0 | 0 |
|   |   | Post | 4 | 5 | 4 | 3 | 0 | 0 | 0 | 5 | 5 | 5 | 4 | 5 | — | 5 | 5 | 0 | 3 | 1 | 4 | 4 | 3 | 0 | 0 |
| 12 | 0.05 | Pre | 0 | 0 | 0 | 0 | 0 | — | 0 | 0 | 0 | 0 | 0 | 0 | 0 | 0 | — | 0 | 0 | 0 | 0 | 0 | — | 0 | 0 |
|   |   | Post | 2 | — | — | 3 | 0 | — | 3 | 3 | 3 | — | 2 | 4 | 5 | 2 | 2 | 0 | 0 | — | 0 | — | 0 | 0 | 0 |
| 20 | 5.0 | Pre | 5 | 2 | 4 | 4 | 0 | 1 | 0 | 3 | 2 | 0 | 4 | 2 | 5 | 5 | — | 0 | 0 | 0 | 1 | 1 | — | — | 0 |
|   |   | Post | 5 | 4 | 5 | 4 | 2 | 2 | 4 | 5 | 5 | 5 | 5 | 5 | 5 | 5 | 5 | 3 | 3 | 3 | 5 | 5 | 3 | 2 | 0 |
| 21 | 5.0 | Pre | 4 | 0 | 0 | 0 | 0 | 0 | 0 | 0 | 0 | 0 | 0 | 1 | 0 | 5 | — | 0 | 0 | 0 | 0 | 0 | 0 | 0 | 0 |
|   |   | Post | 5 | — | 3 | 4 | 1 | 2 | 1 | 5 | 5 | 4 | 5 | 4 | 5 | 5 | 5 | 3 | 3 | 3 | 3 | 4 | — | 1 | 0 |
| 22 | 5.0 | Pre | 0 | 0 | 0 | 0 | 0 | 0 | 0 | 0 | 0 | 0 | 1 | 0 | 2 | 3 | — | 0 | 2 | 2 | 1 | 0 | 0 | 0 | 0 |
|   |   | Post | 4 | 4 | 4 | 4 | 0 | 2 | 2 | 5 | 4 | 4 | 4 | 4 | 3 | 3 | 4 | 2 | 1 | 2 | 0 | 2 | 0 | 0 | 0 |
| 23 | 4.0 | Pre | 4 | 0 | 0 | 0 | 0 | 0 | 0 | 0 | 0 | 0 | 0 | 0 | 0 | 0 | — | 0 | 0 | — | 0 | 0 | 0 | 0 | 0 |
|   |   | Post | 5 | 4 | 0 | 4 | 0 | 0 | — | 5 | 5 | 5 | 4 | 5 | 5 | 4 | 4 | 0 | 0 | 0 | 2 | 3 | 1 | 1 | 0 |
| 24 | 4.0 | Post | 5 | 4 | 3 | 1 | 0 | 0 | 0 | 4 | 0 | 5 | 5 | 4 | 5 | 3 | 2 | 0 | 0 | 0 | 0 | 0 | 0 | 0 | 0 |

Names of test plants in Table III
Sb Sugar beet
Rp Rape
Ct Cotton
Sy Soya bean
Mz Maize
Ww Winter wheat
Rc Rice
Sn Senecio vulgaris
Ip Ipomoea purpurea
Am Amaranthus retroflexus
Pi Polygonum aviculare
Ca Chenopodium album
Po Portulaca oleracea
Ab Abutilon theophrastii
Cv Convolvulus arvensis
Ot/Av As in Example I
Dg Digitaria sanguinalis
Pu Poa annua
St Setaria viridis
Ec Echinochloa crus-galli
Sh Sorghum halepense
Ag Agropyron repens
Cp Cyperus rotundus This Example illustrates the herbicidal properties of compounds used in the invention in relation to a wider range of test plants than in Example 1. Tests were carried out in a similar way to those of Example 1, but using a lower application rate. The compounds were formulated by mixing the appropriate amount of each compound with 5 ml of an emulsion prepared by diluting 160 ml of a solution containing 21.8 grams per liter of Span 80 and 78.2 grams per liter of Tween 20 in methylcyclohexanone to 500 ml with water. The mixture of the compound and the emulsion was shaken with glass beads and diluted to 40 ml with water. Damage to plants was assessed on a scale of 0 to 5 where 0 is 0 to 20% damage and 5 is complete kill. In the table of results, a dash (—) means that no test was made. The results are given in Table III below.

EXAMPLE 3

This Example illustrates the herbicidal properties of Compound No. 1 of Table I against a range of test plants. The tests were carried out in general as described in Example 1, with a small change in the pre-emergence test. In this test, the seeds of the test plants were sown in a shallow slit formed in the soil, and the surface levelled and sprayed. Fresh soil was then spread thinly over the sprayed surface. Results are expressed on a scale of 0 to 9 where 0 is 0 to 11% damage and 9 is complete kill.

The results are given in Tables IV, V and VI below.

TABLE IV

| APPLICATION RATE KG/HA | PRE- OR POST-EMERGENCE APPLICATION | TEST PLANTS | | | | | | | | | |
|---|---|---|---|---|---|---|---|---|---|---|---|
| | | Ww | Br | Pe | Fb | Av | Al | Sm | Ca | Pi | Tm |
| 1 | Pre | 0 | 0 | 0 | 0 | 0 | 0 | 0 | 3 | 0 | 0 |
|   | Post | 0 | 0 | 1 | 1 | 0 | 1 | 9 | 9 | 9 | 9 |
| 4 | Pre | 0 | 0 | 0 | 0 | 0 | 0 | 8 | 8 | — | 2 |

TABLE IV-continued

| APPLICATION RATE KG/HA | PRE- OR POST-EMERGENCE APPLICATION | TEST PLANTS | | | | | | | | | |
|---|---|---|---|---|---|---|---|---|---|---|---|
| | | Ww | Br | Pe | Fb | Av | Al | Sm | Ca | Pi | Tm |
| | Post | 7 | 3 | 8 | 8 | 7 | 7 | 9 | 9 | 9 | 9 |

TABLE V

| APPLICATION RATE KG/HA | PRE- OR POST-EMERGENCE APPLICATION | TEST PLANTS | | | | | | | | | |
|---|---|---|---|---|---|---|---|---|---|---|---|
| | | Rp | Sb | Sr | To | Al | Sm | Ca | Pl | Sn | Sp |
| 1 | Pre | 0 | 5 | 0 | 0 | 0 | 0 | 1 | 0 | 0 | 0 |
| 1 | Post | 8 | 9 | 6 | 9 | 0 | 9 | 9 | 7 | 9 | 9 |
| 4 | Pre | 3 | 9 | 3 | 1 | 3 | 7 | 5 | 4 | 8 | 0 |
| 4 | Post | 9 | 9 | 9 | 9 | 2 | 9 | 9 | 9 | 9 | 9 |

TABLE VI

| APPLICATION RATE KG/HA | PRE- OR POST-EMERGENCE APPLICATION | TEST PLANTS | | | | | | | | | | | |
|---|---|---|---|---|---|---|---|---|---|---|---|---|---|
| | | Sy | Ct | Mz | Rc | Sg | Ei | Ec | Dg | St | Sf | Sh | Cn | Am |
| 1 | Pre | 0 | 0 | 0 | 0 | 0 | 0 | 0 | 0 | 0 | 0 | 0 | 0 |
| 1 | Post | 1 | 1 | 0 | 0 | 0 | 0 | 0 | 0 | 0 | 0 | 0 | 7 |
| 4 | Pre | 0 | 0 | 0 | 0 | 0 | 0 | 0 | 0 | 0 | 0 | 0 | 1 |
| 4 | Post | 1 | 2 | 0 | 7 | 1 | 3 | 4 | 2 | 2 | 3 | 3 | 1 | 9 |

The results in Table VI are for assessments made 26 days after treatment.

Names of test plants in Tables IV, V and VI

Br Barley
Pe Pea
Fb Field beans
Al *Alopecurus myosuroides*
Sm *Stellaria media*
Pi *Polygonum aviculare*
Tm *Tripleurospermum maritimum inodorum*
Sr Sunflower
To Tomato
Pl *Polygonum persicaria*
Sp *Sinapis arvensis*
Sg Sorghum
Ei *Eleusine indica*
Sf *Setaria faberii*
Sh *Sorghum halepense*

EXAMPLE 4

This Example illustrates the preparation of Compound no. 1 of Table I by the method of Scheme A.

2-Amino-5-isopropyl-1,2,4-triazole (3.5 g) was dissolved in dry pyridine (40 ml) and methyl N-chlorocarbonyl-N-isopropylurethane (5.0 g) was added dropwise. The mixture was stirred for 2 hours at room temperature. The excess of pyridine was evaporated in a vacuum and the remaining oil was taken up in chloroform and washed three times with water (3 × 50 ml). The chloroform solution was dried and evaporated to yield a white solid. Recrystallisation from light petroleum (b.p. 80–100° C) gave compound no. 1 of Table I having a melting point of 156–159° C.

EXAMPLE 5

This Example illustrates the preparation of compound no. 4 of Table I by the method of Scheme B.

Isopropyl isocyanate (10 g) was added dropwise to a stirred solution of 2-amino-5-methyl-1,2,4-triazole (3.92 g) in dry pyridine (50 ml) at room temperature. When addition was complete the solution was heated under reflux for 17 hours. The excess of pyridine was removed in a vacuum and the remaining solid extracted with aqueous sodium carbonate solution. The aqueous extracts were acidified with 2 molar hydrochloric acid and the mixture extracted with chloroform. The chloroform extracts were dried and evaporated under reduced pressure. The residue was recrystallised from a mixture of toluene and petroleum to give compound no. 4 of Table I, having a melting point of 202° C.

EXAMPLE 6

This Example illustrates the herbicidal properties of Compound no. 4 of Table I against a range of test plants. The tests were carried out as in Example 3 and the results are given in Tables VII, VIII and IX below:

TABLE VII

| APPLICATION RATE KG/HA | PRE- OR POST-EMERGENCE APPLICATION | TEST PLANTS | | | | | | | | | | | | | | |
|---|---|---|---|---|---|---|---|---|---|---|---|---|---|---|---|---|
| | | Ww | Br | Pe | Rp | Sb | Le | Av | Al | Bt | Ag | Sm | Ca | Pi | Tm | Sp |
| 1 | Pre | 0 | 0 | 0 | 0 | 2 | 1 | 1 | 0 | 0 | 0 | 1 | 2 | 1 | 1 | 1 |
| 1 | Post | 0 | 0 | 9 | 9 | 9 | 9 | 8 | 2 | 2 | 0 | 9 | 9 | 9 | 9 | 9 |
| 4 | Pre | 4 | 2 | 8 | 9 | 9 | 9 | 9 | 5 | 4 | 2 | 9 | 7 | 9 | 8 | 6 |
| 4 | Post | 7 | 2 | 9 | 7 | 9 | 9 | 9 | 7 | 6 | 4 | 9 | 9 | 9 | 9 | 9 |

TABLE VIII

| APPLICATION RATE KG/HA | PRE- OR POST-EMERGENCE APPLICATION | TEST PLANTS | | | | | | | | | | | | | | |
|---|---|---|---|---|---|---|---|---|---|---|---|---|---|---|---|---|
| | | Mz | Sy | Gn | Ct | To | Po | Am | Ip | Dt | Ab | Se | Co | Si | Ds | Xa |
| 1 | Pre | 0 | 0 | 0 | 0 | 0 | 6 | 7 | 2 | 3 | 3 | 6 | 4 | 1 | 1 | — |
| 1 | Post | 0 | 8 | 0 | 9 | 9 | 9 | 9 | 9 | 9 | 9 | 9 | 9 | 9 | 9 | — |
| 4 | Pre | 1 | 8 | 0 | 0 | 4 | 9 | 9 | 4 | 8 | 7 | 9 | 9 | 8 | 8 | — |

TABLE VIII-continued

| APPLICATION RATE KG/HA | PRE- OR POST-EMERGENCE APPLICATION | TEST PLANTS | | | | | | | | | | | | | |
|---|---|---|---|---|---|---|---|---|---|---|---|---|---|---|---|
| | | Mz | Sy | Gn | Ct | To | Po | Am | Ip | Dt | Ab | Se | Co | Si | Ds | Xa |
| | Post | 0 | 9 | 0 | 9 | 9 | 9 | 9 | 9 | 9 | 9 | 9 | 9 | 9 | 9 | 9 |

TABLE IX

| APPLICATION RATE KG/HA | PRE- OR POST-EMERGENCE APPLICATION | TEST PLANTS | | | | | | | | | | | | | |
|---|---|---|---|---|---|---|---|---|---|---|---|---|---|---|
| | | Sy | Ct | Mz | Rc | Sg | Ei | Ec | Dg | St | Sf | Sh | Cp | Am | Pm |
| 0.75 | | 0 | 0 | 0 | 0 | 0 | 1 | 1 | 0 | 0 | 0 | 0 | 5 | 2 | |
| | | 8 | 9 | 0 | 2 | 3 | 9 | 9 | 9 | 9 | 9 | 6 | 1 | 9 | 8 |
| 3.0 | | 5 | 3 | 0 | 3 | 0 | 6 | 7 | 8 | 8 | 5 | 6 | 1 | 8 | 5 |
| | | 9 | 9 | 0 | 7 | 8 | 9 | 9 | 9 | 9 | 9 | 9 | 3 | 9 | 9 |

The names of the test plants are set forth in Examples 1, 2 and 3 with the exception of the following:
Bt *Bromus tectorum*
Gn Ground nut
Dt *Desmodium tortuosum*
Se *Sesbania exaltata*
Co *Cassia obtusifolia*
Si *Sida spinosa*
Ds *Datura stramonium*
Xa *Xanthium pennsylvanicum*
Pm *Panicum maximum*

EXAMPLE 7

This Example illustrates a herbicidal composition comprising a dispersible powder containing a triazolotriazine compound according to the invention. The constituents of the composition are as follows:

| Constituent | Percentage by weight |
|---|---|
| Compound no. 4 | 50 |
| Vanicell E | 5 |
| Fenopon T77 | 2 |
| Citric acid | 5 |
| Spestone (china clay) | 38 |

Vanicell E is a Trade Mark for a lignosulphonate dispersant. Fenopon T77 is a Trade Mark for a taurate wetting agent.

This dispersible powder may be applied as a suspension in an aqueous solution containing as surfactants Span 80 (a sorbitan fatty acid ester) in a concentrate of 0.2 grams per liter and Tween 20 (an ethoxylated sorbitan fatty acid ester) in a concentration of 0.8 grams per liter.

EXAMPLE 8

This Example illustrates a method of preparing compound no. 24 of Table I.

3-Amino-5-methylthio-1,2,4-triazole (13.0 g) was added in portions to a stirred solution of N-isopropyl-bis-chloroformylamine (13.4 g) in dry acetonitrile (150 ml). After addition was complete, the mixture was heated under reflux for 6 hours. The reaction mixture was filtered while hot. On standing overnight at 0° C the filtrate deposited a pale yellow solid of melting point 260° C, identified as compound no. 24.

What is claimed is:

1. A process of severely damaging or killing unwanted plants, which comprises applying to the plants, or to the growth medium thereof, a triazolotriazine compound of the formula:

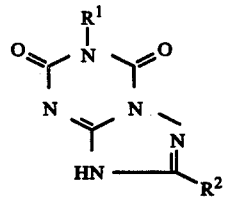

or an agriculturally acceptable salt thereof, wherein $R^1$ is an alkyl or cycloalkyl radical of 1 to 8 carbon atoms, and $R^2$ is a hydrogen atom; an alkyl or cycloalkyl radical of 1 to 6 carbon atoms; an alkylthio radical of 1 to 6 carbon atoms; or a dialkylamino radical wherein the two alkyl radicals each contain from 1 to 6 carbon atoms.

2. A process as claimed in claim 1 in which the triazolotriazine compound is applied as an agriculturally acceptable salt having a cation which is an ammonium ion, an ammonium ion substituted by one, two, three, or four alkyl radicals each of 1 to 6 carbon atoms, an alkali metal cation, or an alkaline earth metal cation.

3. A process as claimed in claim 1 wherein the triazolotriazine compound is applied at the rate of from 0.5 to 10 kilograms per hectare.

4. A process of selectively inhibiting the growth of weeds in crops of wheat and barley, which comprises applying to the area of the crop a triazolotriazine compound as defined in claim 1, in an amount sufficient to inhibit the growth of the weeds, but insufficient to damage the crop substantially.

5. A process as claimed in claim 4 wherein the triazolotriazine compound is applied at the rate of 0.5 to 5 kilograms per hectare.

6. Herbicidal compositions, comprising as an active ingredient a triazolotriazine compound as defined in claim 1, in admixture with a carrier comprising a solid or liquid diluent.

7. Herbicidal compositions as claimed in claim 6 which further comprise a surface-active agent.

8. Herbicidal compositions as claimed in claim 7, comprising an aqueous solution of an alkali metal salt of a triazolotriazine compound as defined in claim 1.

9. Triazolotriazine compounds of the formula:

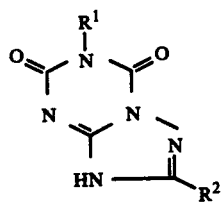

and salts thereof, wherein $R^1$ is an alkyl or cycloalkyl radical of 1 to 8 carbon atoms, and $R^2$ is a hydrogen atom; an alkyl or cycloalkyl radical of 1 to 6 carbon atoms; or a dialkylamino radical wherein the two alkyl radicals each contain from 1 to 6 carbon atoms.

10. A triazolotriazine compound as claimed in claim 9, wherein $R^1$ and $R^2$ are both isopropyl radicals, or wherein $R^1$ is an isopropyl radical and $R^2$ is a methyl radical.

* * * * *